US00PP18598P3

(12) United States Plant Patent
Tous

(10) Patent No.: US PP18,598 P3
(45) Date of Patent: Mar. 18, 2008

(54) OLIVE TREE, 'ARBOSANA OLINT'

(50) Latin Name: *Olea europaea*
Varietal Denomination: Arbosana Olint

(76) Inventor: Joan Tous, 612 E. Gridley Road, Gridley, CA (US) 95948

( * ) Notice: Subject to any disclaimer, the term of this patent is extended or adjusted under 35 U.S.C. 154(b) by 0 days.

(21) Appl. No.: 11/093,397

(22) Filed: Mar. 29, 2005

(65) Prior Publication Data

US 2006/0225167 P1 Oct. 5, 2006

(51) Int. Cl.
*A01H 5/00* (2006.01)

(52) U.S. Cl. ..... Plt./158
(58) Field of Classification Search ..... Plt./158
See application file for complete search history.

(56) References Cited

U.S. PATENT DOCUMENTS

| | | | |
|---|---|---|---|
| PP5,829 | P | 12/1986 | Haas |
| PP7,750 | P | 12/1991 | Zampini |
| PP10,641 | P | 10/1998 | Sonnoli, Jr. |
| PP13,077 | P2 | 10/2002 | Fontanazza |

OTHER PUBLICATIONS

Garden Web Glossary of Botanical Terms [online], retrieved on Jan. 8, 2007. Retrieved from the Internet <http://glossary.gardenweb.com/glossary/> 3 pages.*

The New Royal Horticultural Society Dictionary of Gardening, 1992, vol. 3, p. 354.*

Tous et al. Arbosana Irta–i–43, Catalonia Agroinifora Journal, No. 2, Aug. 2000 pp. 13, 15.*

IRTA [online], [retrieved on Apr. 8, 2006]. Retrieved from the Internet <http://www.irta.es/eng/index.html>, 4 pages.*

The Olive Oil Source, California Olive Oil News, Jul. 2002, vol. 5, Issue 7 [online], [retrieved on Dec. 5, 2005]. Retrieved from the Internet <http://www.oliveoilsource.com/newsletter/olivenews5–7.htm> 10 pages.*

* cited by examiner

*Primary Examiner*—Kent Bell
*Assistant Examiner*—June Hwu
(74) *Attorney, Agent, or Firm*—Mark D. Miller

(57) ABSTRACT

The present invention comprises a new and distinct clonal system of *Olea europaea* cultivar 'Arbosana OLINT'. This new invention possesses all of the resistance to olive knot and cold temperature while producing an excellent commercial crop within three to four years in the Sacramento Valley of northern California, and is primarily grown for olive oil production. The dense planting and comparatively small height provides for mechanical harvesting with a very good to excellent level of production. The plants are ideally suited for olive oil production, mechanical harvesting and high density planting. The fruit matures in northern California during the fourth week of October.

5 Drawing Sheets

Olive tree: (*Olea europaea*).

BACKGROUND OF THE NEW VARIETY

The present invention relates to a new and distinct variety of olive plant, *Olea europaea,* and will hereafter be denominated varietally as 'Arbosana OLINT' and more particularly to an olive plant that produces fruit for harvest during the fourth week of October in the Gridley area of the northern Sacramento Valley in California and which is further distinguished as to novelty by having high productivity and very good olive oil yield (19-20%) within three to four years, as well as resistance to low temperature, leaf drop, and olive knot (*Pseudomonas savastoni*).

This new invention relates to a new and distinct variety of olive tree from which a clonal selection (naturally occurring mutation) was originally identified from an olive orchard located in Arbo del Penedes in Spain. The plant was first selected from the orchard in 1989 and then was vegetatively propagated (asexual) in 1991 and brought into the Institute of Research and Technology for Agriculture and Food located at Centre Demas Bove, Apartat 415 43280 Reus, Spain. The clonal selection from the variety 'Arbosana Standard' (unpatented) possessed a branching pattern in which the branching occurs higher up on the trunk and is more upright, resulting in superior production, also uniformly in ripening with superior olive oil quality and quantity.

ORIGIN AND ASEXUAL REPRODUCTION OF THE NEW VARIETY

This new variety has been asexually reproduced, dry cuttings, at the site stated above, in Spain. After verification of the superior characteristics in production, uniformity, olive oil production and quality; vegetatively reproduced cuttings were sent to the USA in 1997. Upon completion of post entry quarantine requirements in Oregon, vegetatively propagated cuttings of this new variety were shipped to Gridley, Calif. where additional cuttings were asexually propagated. In all cases the reproduced plants exhibited the distinguishing characteristics of the original clonal selection.

SUMMARY OF THE NEW VARIETY

The new variety of olive was discovered through a selection process from olive orchards growing in Arbo del Penedes, Spain in the 'Arbosana Standard' variety (unpatented). Through a selection and evaluation process beginning in 1986 that was conducted over an eleven year period at which time the final clonal selection process was completed. Since this new variety is a small tree, usage is primarily for high density plantings (e.g., approximately 670 trees/acre). The new variety possesses the characteristics of resistance to low temperature, and leaf drop as well as olive knot (*Pseudomonas savastoni*). The new variety is late maturing during the fourth week of October, with high productivity and very good olive oil yield (19-20%) within three to four years. This rapid maturity compared to the common varieties grown in California ('Mission,' 'Sevillono' and 'Ascolano') takes about half the time to reach commercial production.

DETAILED DESCRIPTION

Figure 1:
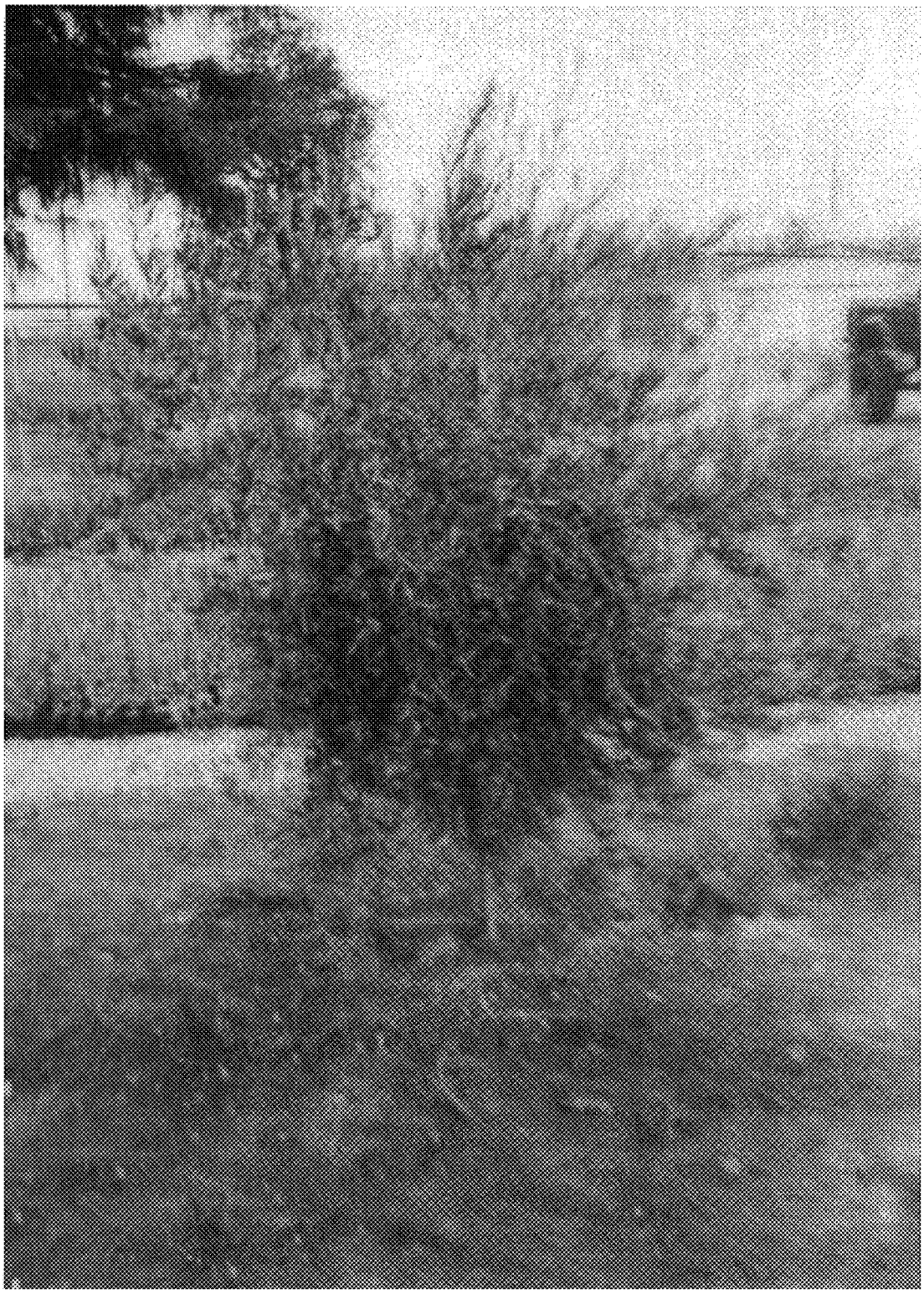
FIG. 1 is a color photograph of the new variety displaying the overall shape of a three year old tree.
Figure 2:
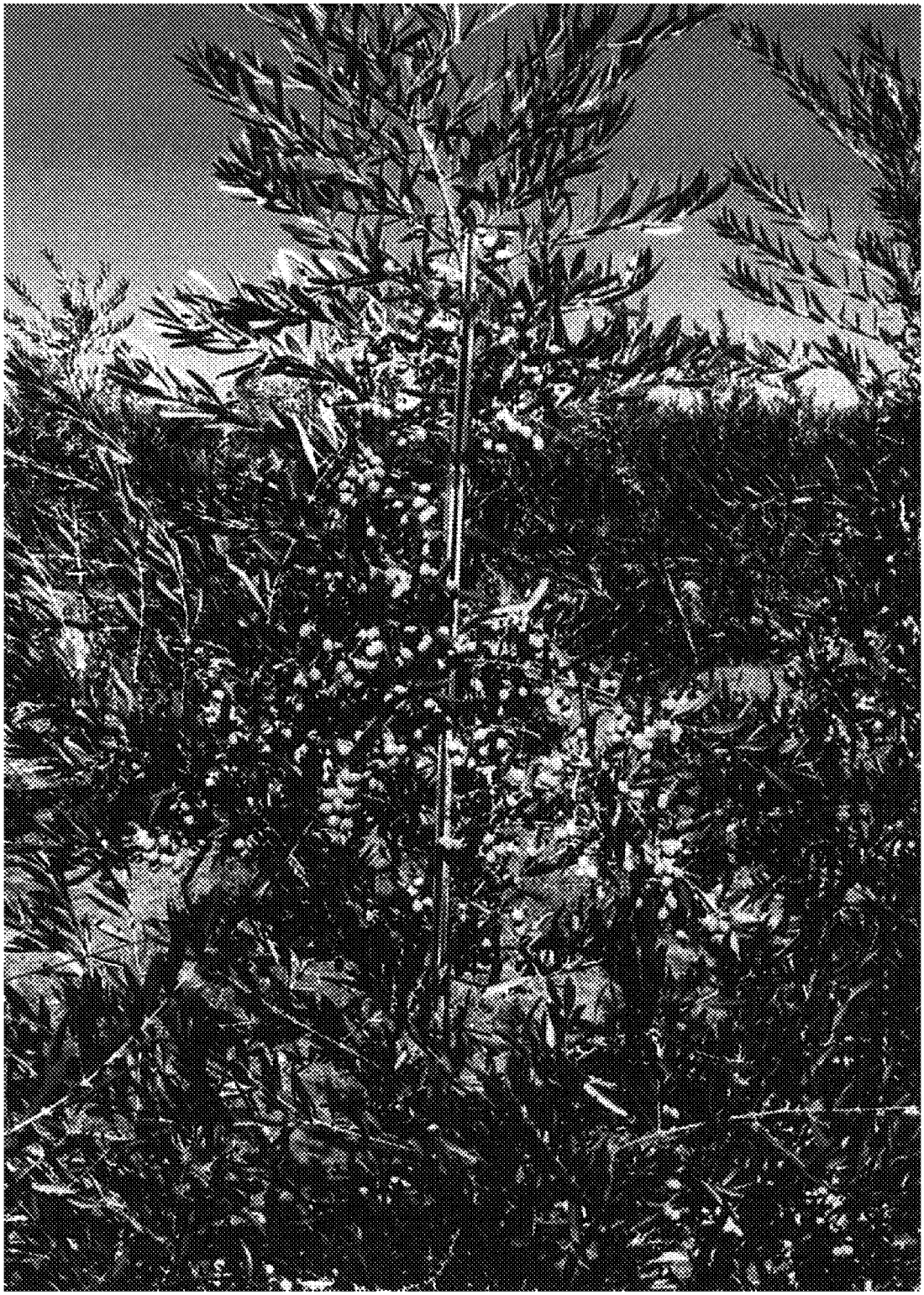
FIG. 2 is a color photograph of the new invention showing it in the third leaf displaying it semi-erect in appearance.
Figure 3:
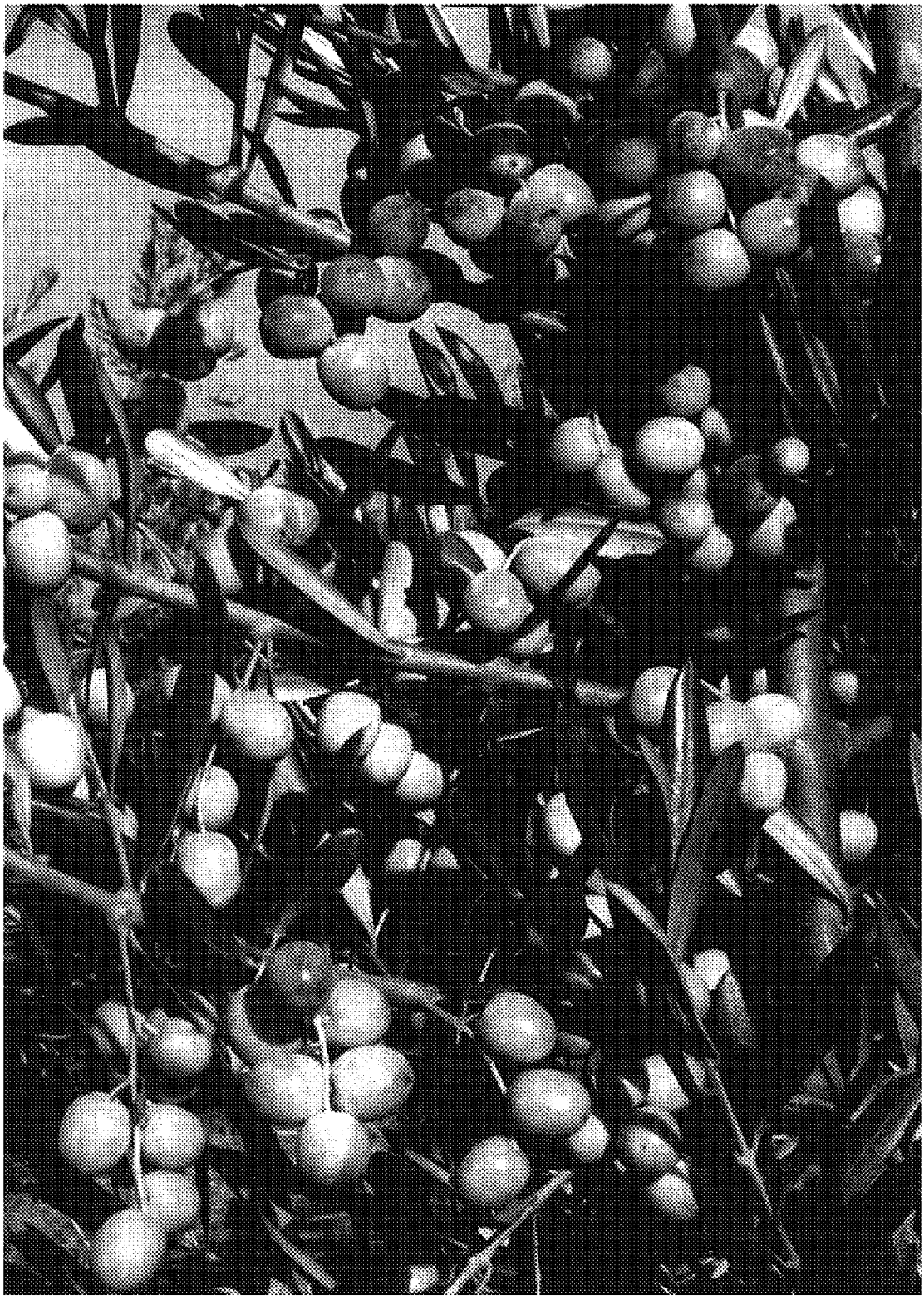
FIG. 3 is a color photograph of a typical branch bearing fruit in clusters of 3-5.
Figure 4:
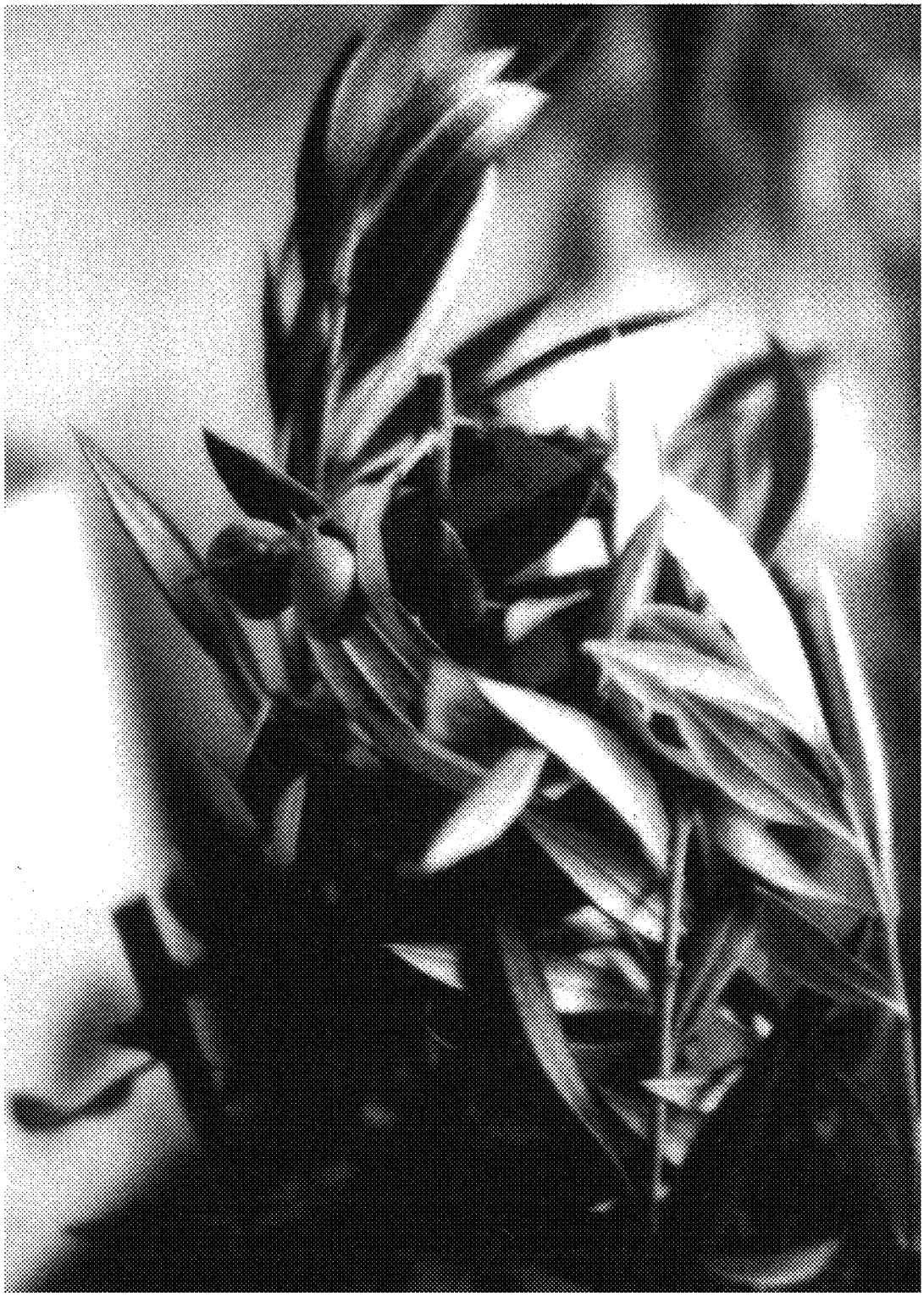
FIG. 4 is a color photograph of the variety displaying upper and lower leaf surfaces.
Figure 5:
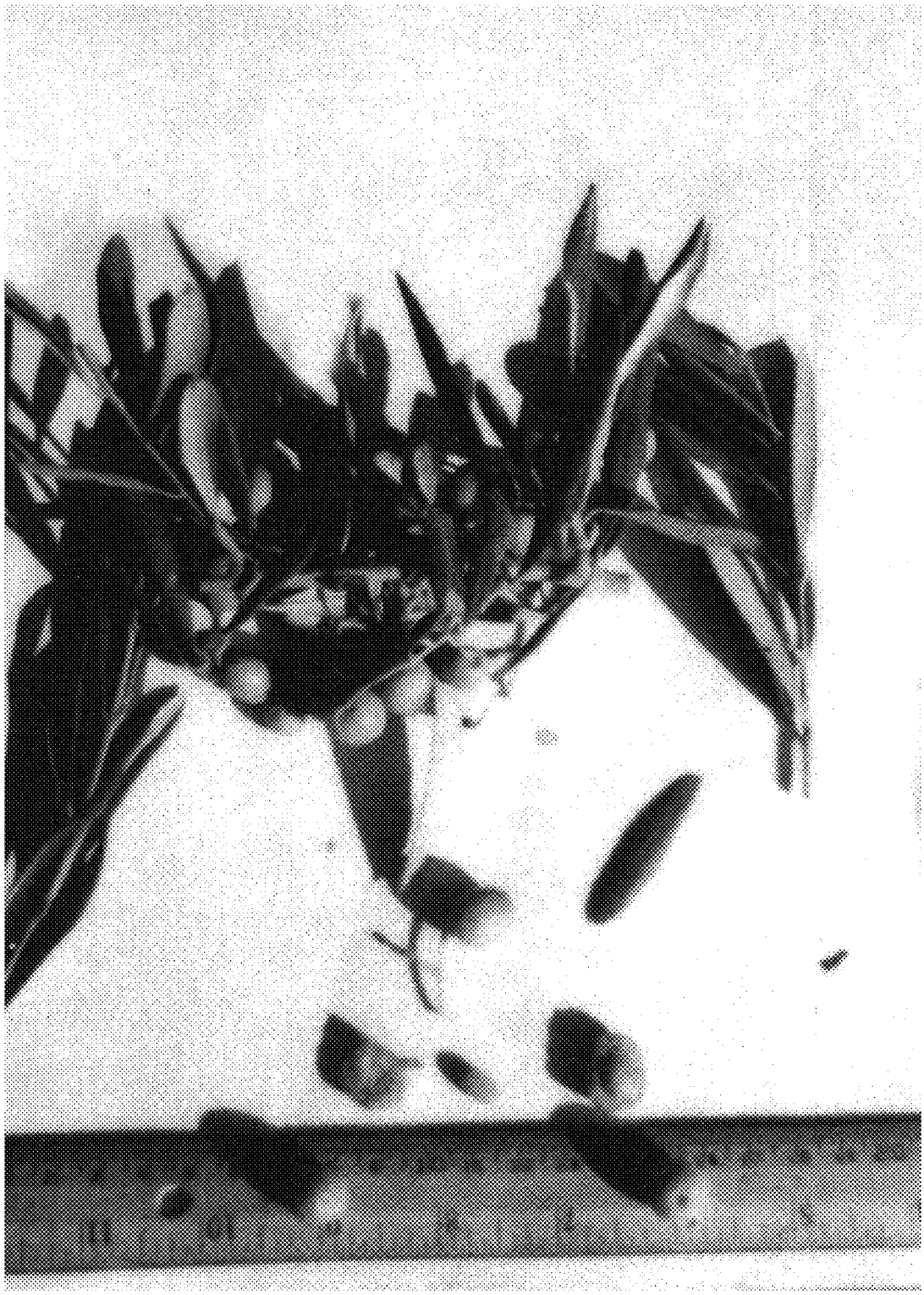
FIG. 5 is a color photograph showing foliage at the top; in the middle a fruit cut in half displaying the flesh and the empty seed cavity on the left, the seed in the middle, the second half of the fruit with the seed in place on the right; and in the bottom of the photograph is a side view of the fruit on the left and the stem end of the fruit on the right on a ruler for scale.

Referring more specifically to the horticultural details of the new and distinct variety of olive trees, the following descriptions have been observed under the ecological details prevailing at the site of origin which is located near Gridley, Calif. in the Sacramento Valley of northern California. The age of the observed plant was 4 years. All major color designations are by reference to the Dictionary of color by Maerz & Paul, First Edition, 1930. Common colors are also employed.

TREE

This new invention has small trees:
- *Height.*—5-6 feet (152-183 cm).
- *Width.*—2.5-3 feet (76-91 cm).
- *Vigor.*—Low.
- *Chilling requirements.*—Normal for olives.
- *Figure.*—Open.
- *Productivity.*—Production level is uniform, with very good distribution through the branches, and good oil production.
- *Regularity of bearing.*—Alternate.

TRUNK

Size: 5 inch (13 cm) circumference, 13 inches (33 cm) above ground.
Surface texture: Smooth.
Color code: Wild Iris (44-B-5).
- *Branches.*—Size: small, 3-4 inches (8-10 cm) circumference at approximately 3 years.
- *Surface texture.*—Mature: smooth. Immature: smooth.
- *Color.*—One year or older: Dusty Green (22-C-1). Immature: Light Grey (36-A-1).
- *Lenticels.*—Number: Many. Small: less than 1 mm (0.04 inch).

LEAVES

Size: Small, opposite.
Length: 58-70 mm (2.26-2.73 in.).
- *Average.*—64 mm (2.50 inches).

Width: 11-12 mm (0.43-47 in.) avg. 11.66 mm (0.46 inch).
Shape: Elliptic and nearly symmetrical.
Margin: Entire.
Apex: Acute.
Base: Cuneate.
Surface texture:
- *Upwardly disposed surface.*—Smooth.
- *Downwardly disposed surface.*—Slightly pubescent.

Color:
- *Upper disposed surface.*—Chrome Green (22-L-12).
- *Downwardly disposed surface.*—Chrysolite Green (19-K-3).

Leaf vein:
- *Color.*—Chrysolite Green (19-K-3).
- *Thickness.*—1 mm (0.04 in.).

Granular characteristics: None.
Petiole: Short, 5 mm (0.20 in.).
Thickness: 1.5-2 mm (0.06-0.08 in.).
Stem glands: None.

FLOWERS

Flower buds: Small, slightly pubescent.
Average bud size: 2.5-4.0 mm (0.10-0.16 inch).
Date of first bloom: Mid-May, Borne in particle.
- *Size.*—Small, 2.5-4 mm (0.10-0.16 inch).
- *Petals.*—Lobed corolla. Color: White (1-A-1).

Number of florets per inflorescence: 10-16.
Number of sepals: 4.
Number of petals: 4.
Fragrance: Very mild.
Reproductive organs: 1 pistil; 15-25 stamens.
Pollen color: Yellow, Empire Y. (9-K-3).

FRUIT

Date of maturity: 4th week of October.
Size: Small.
Weight: Approximately 3.4 grams.
Diameter: 13-15 mm (0.51-59 in.), average 15 mm (0.59 in.).
Length: 15-18 mm (0.59-0.70 in.), average 17.2 mm (0.671 in.).
Form: Elliptical and symmetrical to slightly symmetrical.
Suture: None.
Stem cavity:
- *Width.*—2 mm (0.08 in.).
- *Depth.*—2 mm (0.08 in.).
- *Length.*—3 mm (0.12 in.).
- *Shape.*—Elliptical.

Stem: Average 4.83 mm (0.19 in.).
- *Caliper.*—Very small.

Apex: Slightly rounded.
Pistil point: Obscure.
Skin:
- *Thickness.*—Less than 1 mm (less than 0.01 in.).
- *Texture.*—Smooth.
- *Tendency to crack.*—None.

Color code:
*Ground color.*—Apple Green (19-J-6).
*Flesh color.*—Oyster Gray (19-A-2).
*Color of surface.*—Oyster Gray (19-A-2).
*Color of pit.*—Oyster Gray (19-A-2).
Juice production: Oil production excellent.
*Flavor.*—Unique.
Ripening: Even.

SEED

Type: Cling.
Fibers: None.
Size: Small, less than 0.5 gram.
*Length.*—10 mm (0.39 in.).
*Width.*—6 mm (0.23 in.).
*Thickness.*—6 mm (0.23 in.).
Form: Elliptical, cross section is round.
Apex: Slightly pointed.
Color (dry): Grayish brown (46-D-3).
Texture: Slightly grooved.
Base: Truncate.
Mucron: Obscure.
Suture: Marked.
Sides: About even.
Ridges: Very faint and uneven.
Tendency to split: None known.
Use: Oil production and in some cases for canning.
Resistance: Yes, to olive knot.
Harvesting: Mechanical harvesting, late October.

OIL

The oil yield is approximately 19-20% when the skin of the fruit is mature green and the flesh is tannish and light green.

TABLE 1

Chemical Analysis of 'Arbosana OLINT' Oil

| Type of Fatty Acid | Percent of Total Oil Content |
|---|---|
| C16:0 Palmitic Acid | 13.4 |
| C16:1 Palmitoleic Acid | 1.3 |
| C18:0 Esteric Acid | 2.0 |
| C18:1 Oleic Acid | 74.0 |
| C18:2 Linoleic Acid | 7.66 |
| C18:3 Linoleic Acid | .9 |

M/P ratio (monosaturated fats/polysaturated fats): 8.9.
Polyphenols (ppm catteic acid): 2.78.
K225 (bitterness): 0.24.
Stability (hours at 248 degrees Fahrenheit): 13.5.

The plant shows resistance to low temperature, leaf drop, and olive knot (*Pseudomonas savastoni*).

What is claimed is:

1. A new distinct olive plant as described and illustrated that is characterized by having the general characteristics of the 'Arbosana Standard' (unpatented) variety but is distinguished therefrom in that it matures rapidly, producing olive oil yields having superior quality and quantity within three to four years, and has resistance to low temperature, leaf drop, and olive knot, with the plants being ideally suited for olive oil production, mechanical harvesting and high density planting, the fruit maturing in northern California in about the fourth week of October.

* * * * *